(12) United States Patent
Lear et al.

(10) Patent No.: US 11,571,203 B2
(45) Date of Patent: Feb. 7, 2023

(54) DEFORMABLE SUTURE BRIDGE HAVING AN INSERT AND METHODS OF MANUFACTURING AND USING SAME

(71) Applicant: SUTUREGARD Medical, Inc., Portland, OR (US)

(72) Inventors: William Lear, Corvalis, OR (US); Daniel A Ladizinsky, Lake Oswego, OR (US); Jennifer Akeroyd, Corvallis, OR (US)

(73) Assignee: SUTUREGARD Medical, Inc., Portland, OR (US)

(*) Notice: Subject to any disclaimer, the term of this patent is extended or adjusted under 35 U.S.C. 154(b) by 522 days.

(21) Appl. No.: 16/721,462

(22) Filed: Dec. 19, 2019

(65) Prior Publication Data

US 2020/0121313 A1  Apr. 23, 2020

Related U.S. Application Data

(63) Continuation of application No. 16/240,127, filed on Jan. 4, 2019, now Pat. No. 10,555,730.

(60) Provisional application No. 62/665,329, filed on May 1, 2018.

(51) Int. Cl.
*A61B 17/04* (2006.01)

(52) U.S. Cl.
CPC ...... *A61B 17/0466* (2013.01); *A61B 17/0401* (2013.01); *A61B 2017/0496* (2013.01)

(58) Field of Classification Search
CPC ........ A61B 17/0466; A61B 2017/0496; A61B 17/08–2017/088; A61B 17/0401
See application file for complete search history.

(56) References Cited

U.S. PATENT DOCUMENTS

| | | | | |
|---|---|---|---|---|
| 6,120,525 A | * | 9/2000 | Westcott | A61B 17/0466 606/216 |
| 6,254,624 B1 | * | 7/2001 | Oddsen | A61B 90/02 606/216 |

* cited by examiner

*Primary Examiner* — Thomas McEvoy
(74) *Attorney, Agent, or Firm* — Wei & Sleman LLP

(57) ABSTRACT

A suture bridge includes an elongated rigid insert including a first material, and a deformable shell including a second material, the second material being different than the first material, the shell at least partially surrounding the rigid insert, the insert and the shell collectively forming a bridge body having a first leg including a first patient contacting surface configured to contact a patient's skin, a second leg spaced from the first leg and including a second patient contacting surface configured to contact the patient's skin, a first support connected to the first leg, a second support connected to the second leg, and a traversing member extending between the first support and the second support, the traversing member being connected to the first support distal the first leg and connected to the second support distal the second leg.

18 Claims, 17 Drawing Sheets

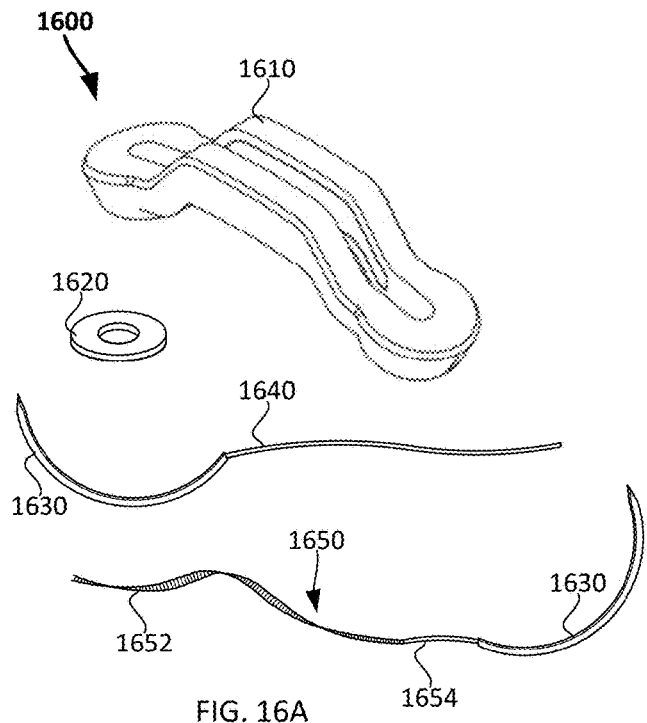
FIG. 16A
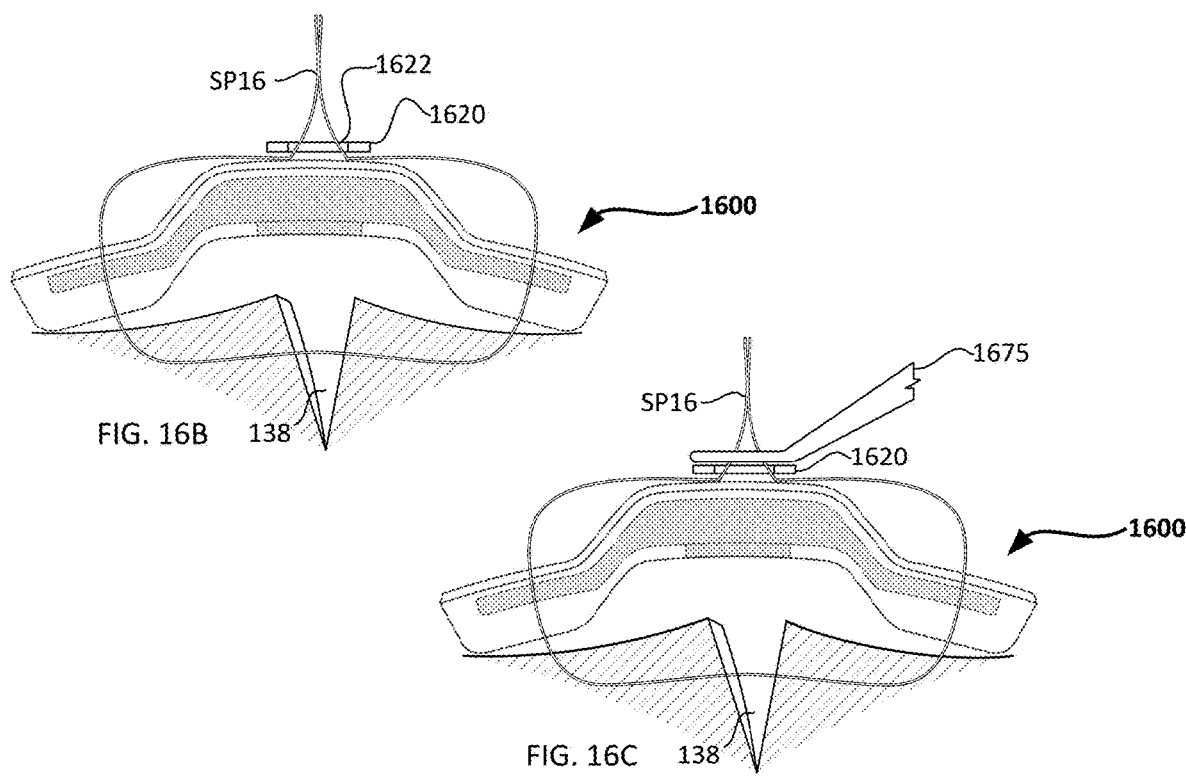
FIG. 16B
FIG. 16C

DEFORMABLE SUTURE BRIDGE HAVING AN INSERT AND METHODS OF MANUFACTURING AND USING SAME

CROSS-REFERENCE TO RELATED APPLICATIONS

This application is a continuation of U.S. patent application Ser. No. 16/240,127, filed Jan. 4, 2019, entitled "DEFORMABLE SUTURE BRIDGE HAVING AN INSERT AND METHODS OF MANUFACTURING AND USING SAME", claims priority to U.S. Provisional Application Ser. No. 62/665,329, filed May 1, 2018, entitled "DEFORMABLE SUTURE BRIDGE HAVING AN INSERT AND METHODS OF MANUFACTURING AND USING SAME," the contents of which are fully incorporated as if fully set forth herein.

FIELD OF THE DISCLOSURE

The present disclosure relates generally to wound closure and methods and devices for improving same. More specifically, the present disclosure relates to a deformable partially elevated suture bridge device and methods for facilitating wound closure.

BACKGROUND OF THE DISCLOSURE

Sutures are stitches used to close open wounds and/or surgical incisions of a patient. A medical practitioner generally uses a needle with an attached thread to substantially sew two adjacent sections of skin together to close the wound or incision. Surgical knots are often used to secure the sutures and ensure proper healing.

Effective surgical knots may be difficult to tie, thereby potentially allowing reopening of the wound or incision. In such cases, the patient may be at risk of infection if the wound or incision reopens. In another example, sutures and surgical knots contacting the skin can be inflammatory and/or become "ingrown" and actually impede healing of the wound or incision.

Additionally, complications may arise if the suture is tied too tightly or too loosely.

For example, wound eversion may be a desired outcome of suture technique, especially in high-tension areas of the skin, such where skin overlies the shoulder, knee, angle of the mandible, etc. Wound eversion occurs when the two wound surfaces are horizontally opposed into one another such that the closed incision is under no tension and topographically lies in a plane above the resting horizontal skin plane. Wound closures with maximal eversion resist excessive widening of the scar due to ongoing ambient stresses in the high-tension area during the wound healing and scar maturation processes. However, wound eversion can be technically difficult to achieve for less skilled operator, and a device to facilitate this is desirable. Further, there may be excessive tension on closures where an excisional defect is present in the skin. When suture is placed under excessive tension to close such wounds, the suture itself can slice through the skin ("cheesewiring"). In this setting, a surgical device interposed between the skin and suture for the purpose of spreading the suture's force over a broader area is desirable. The embodiments in the following descriptions integrate these two important functions into a single device, that is the achievement of maximal wound eversion closure with prevention of suture-induced trauma to the skin. Thus, there exists a need for suture devices that improve upon and advance the design of known suture devices.

SUMMARY OF THE DISCLOSURE

In at least some embodiments, a suture bridge includes an elongated rigid insert including a first material, and a deformable shell including a second material, the second material being different than the first material, the shell at least partially surrounding the rigid insert, the insert and the shell collectively forming a bridge body having a first leg including a first patient contacting surface configured to contact a patient's skin, a second leg spaced from the first leg and including a second patient contacting surface configured to contact the patient's skin, a first support connected to the first leg, a second support connected to the second leg, a first slot at least partially formed through a portion of the first leg, and a portion of the first support, a second slot at least partially formed through a portion of the second leg, and a portion of the second support, and a traversing member extending between the first support and the second support.

BRIEF DESCRIPTION OF THE DISCLOSURE

Various embodiments of the presently disclosed suture bridges are disclosed herein with reference to the drawings, wherein.

Figure 1:
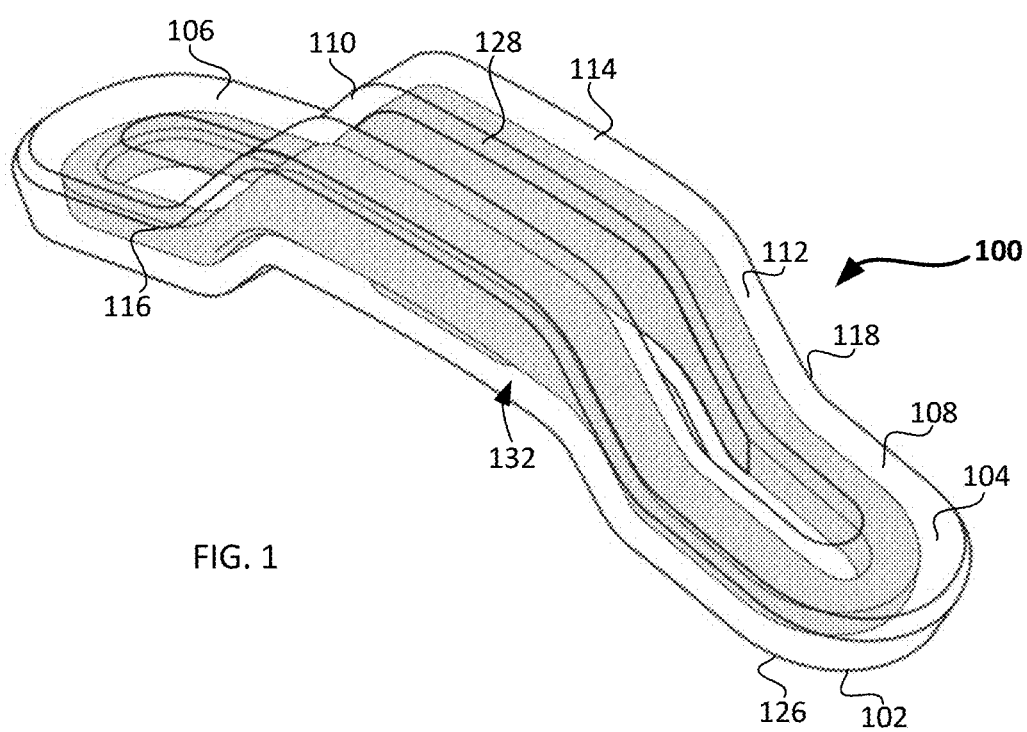
FIG. 1 is a schematic perspective view of a suture bridge according to one embodiment of the present disclosure.
Figure 5A:
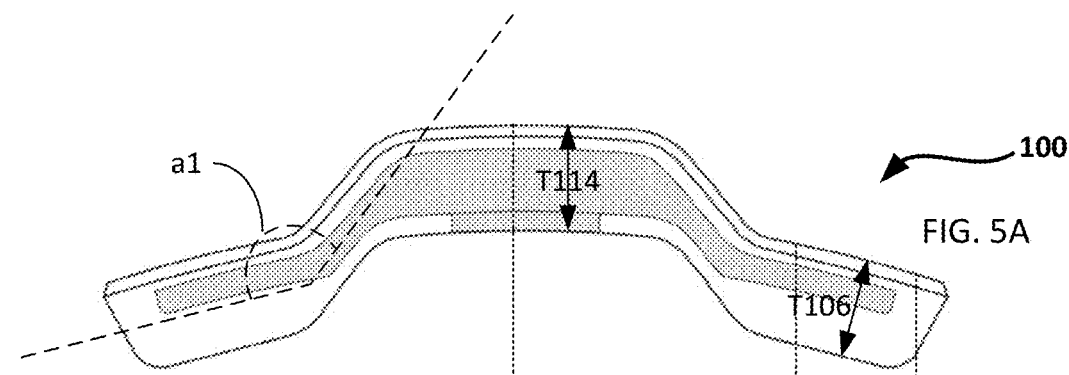
Figure 5B:
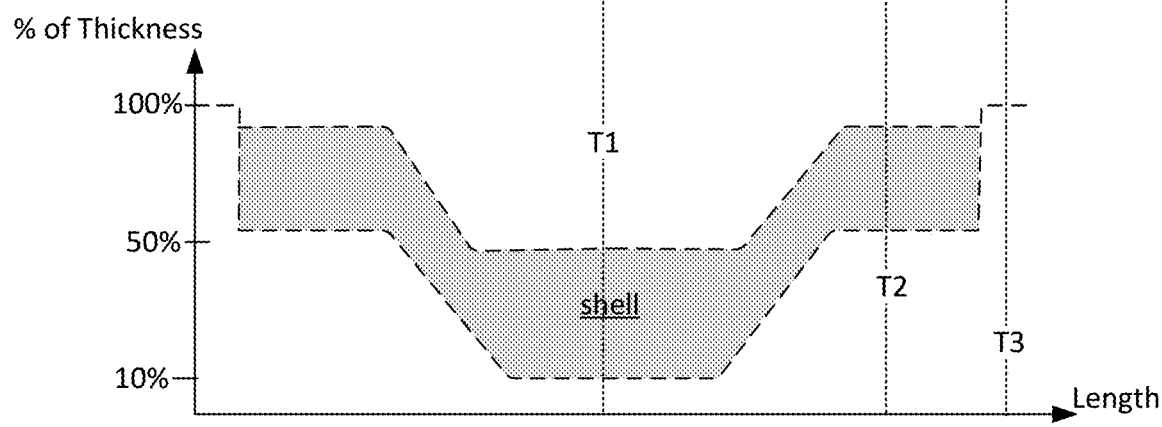
Figure 6A:
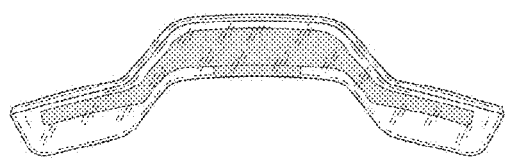
Figure 6B:
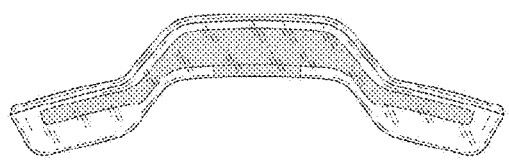
Figure 6C:
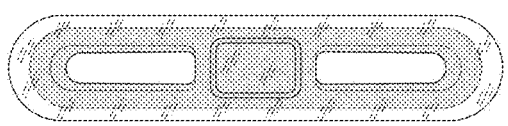
Figure 6D:
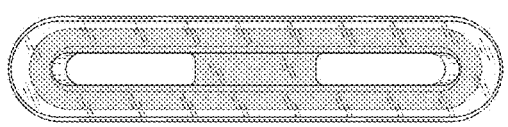
Figure 6E:
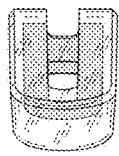
Figure 6F:
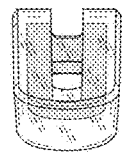
Figure 6G:
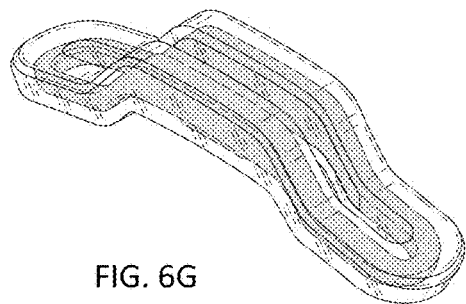
Figure 7A:
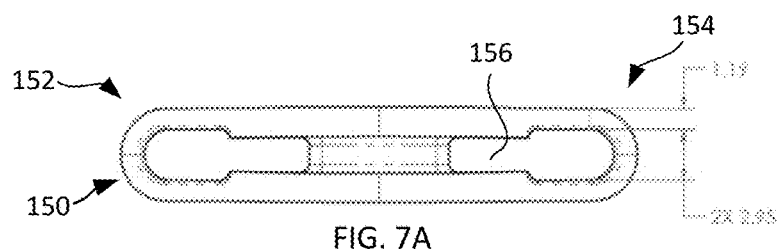
Figure 7B:
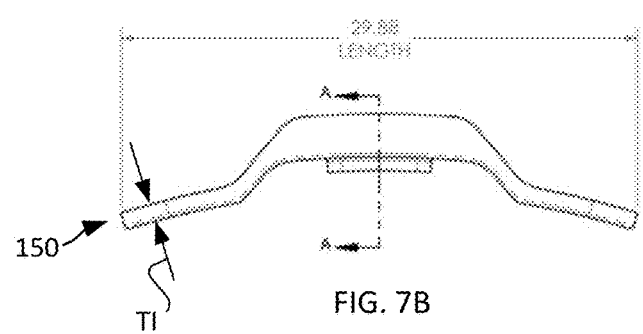
Figures 7D, 7E:
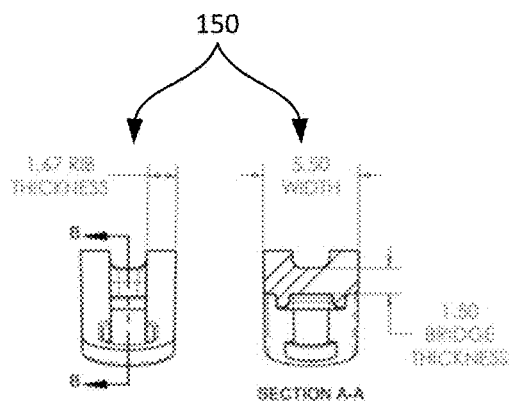
Figure 7C:
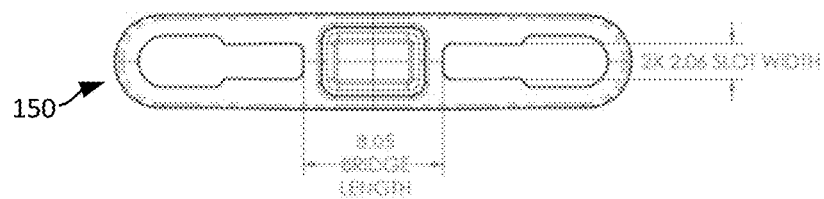
Figure 7F:
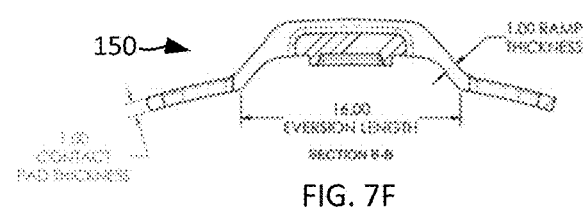
Figure 7G:
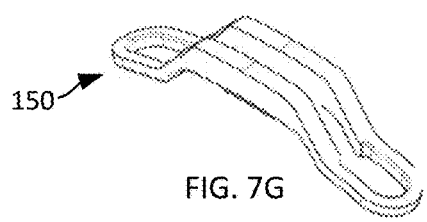
Figure 8A:
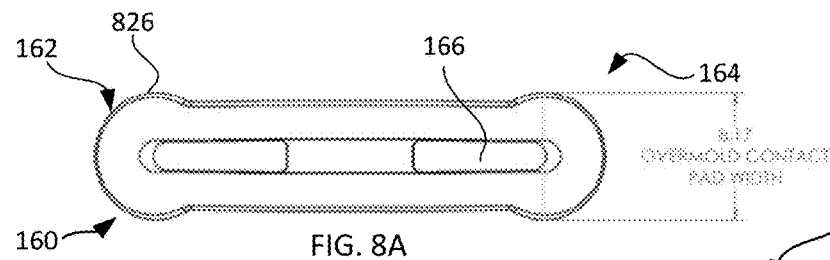
Figure 8B:
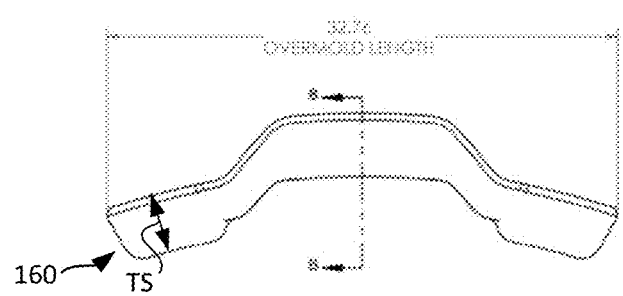
Figures 8D, 8E:
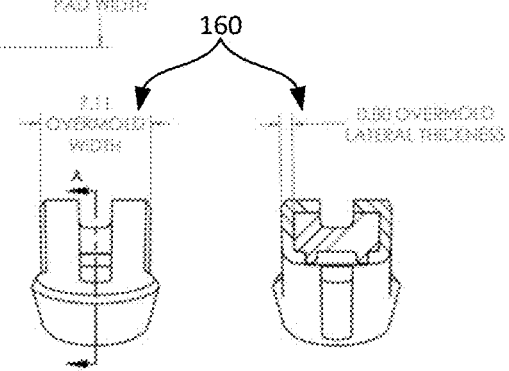
Figure 8C:
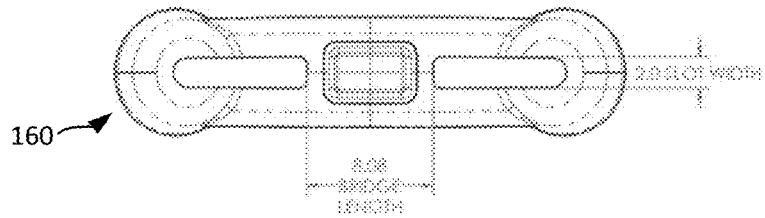
Figure 8F:
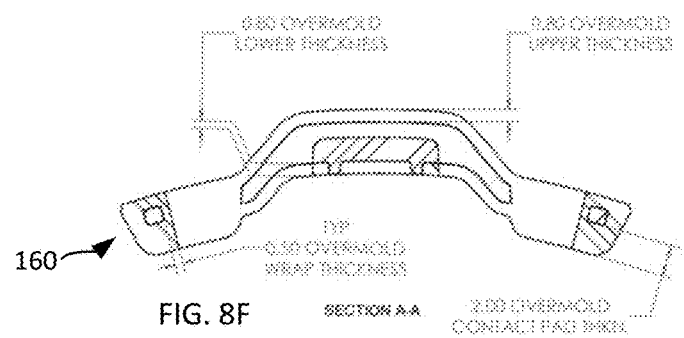
Figure 8G:
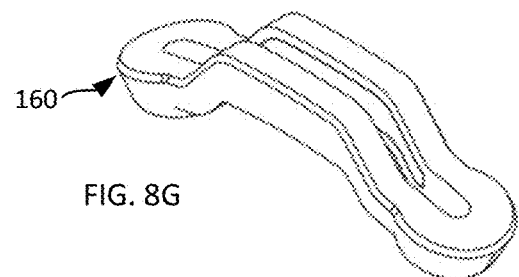
Figure 9A:
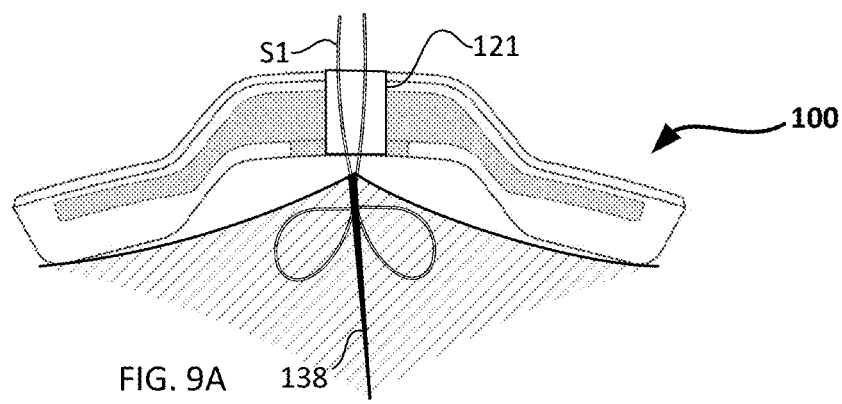
Figure 9B:
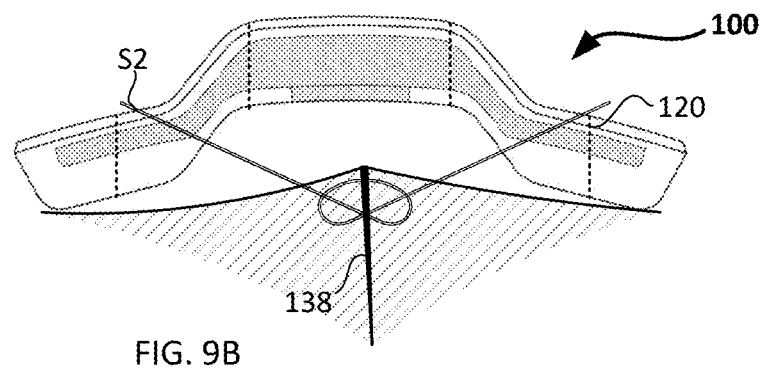
Figure 10A:
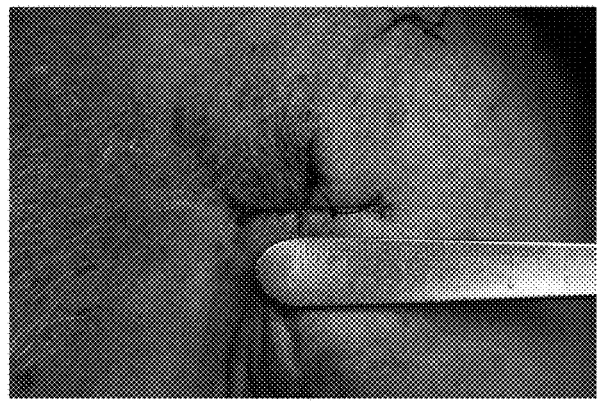
Figure 10B:
Figure 11:
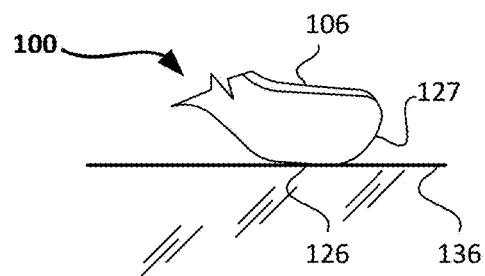
Figure 14A:
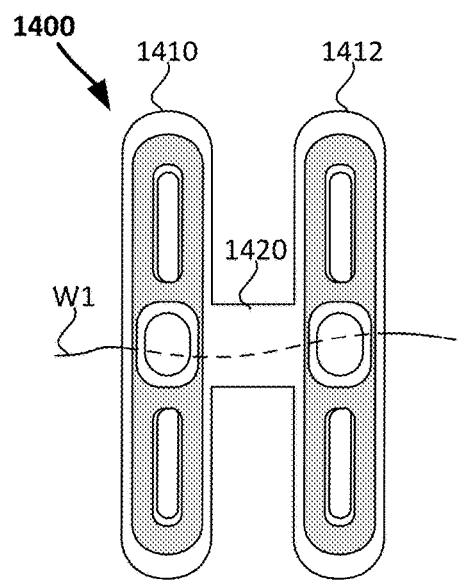
Figure 14B:
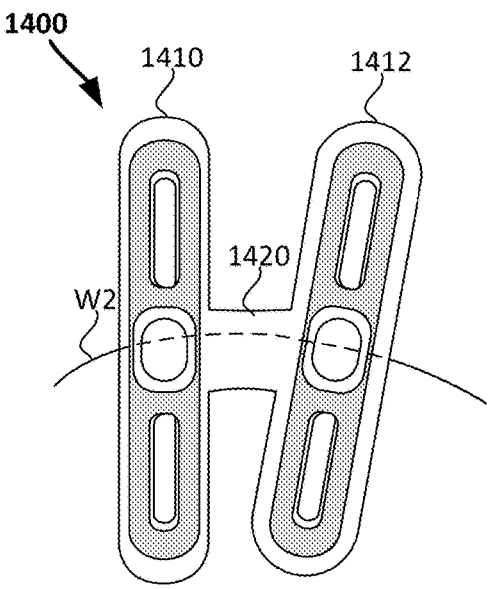
Figure 14C:
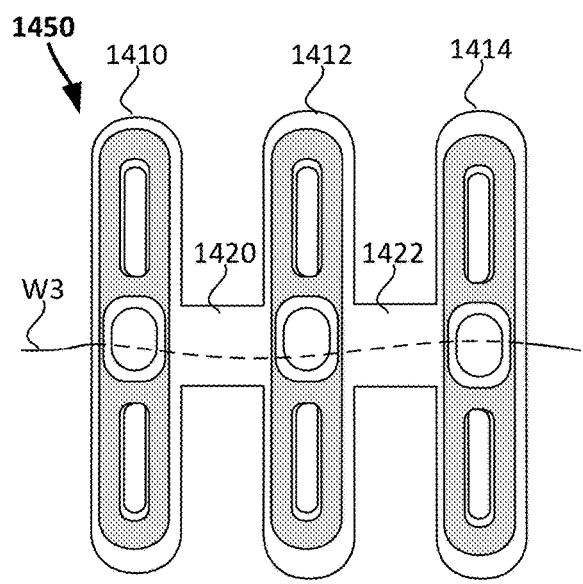
Figure 14D:
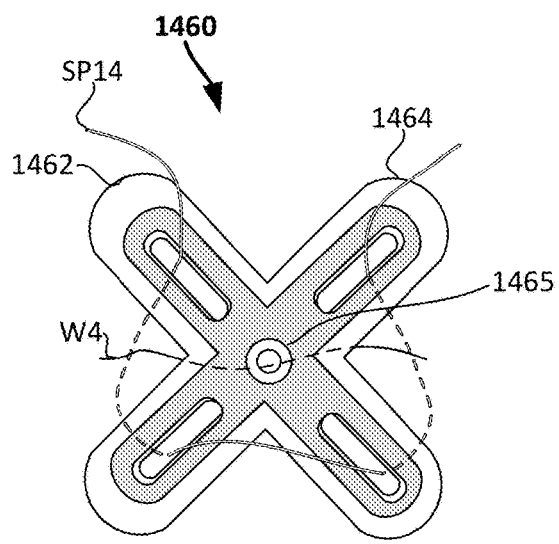
Figure 15A:
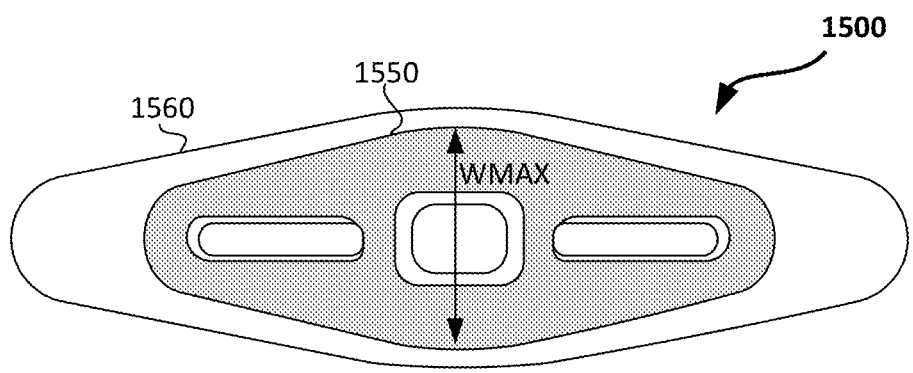
Figure 15B:
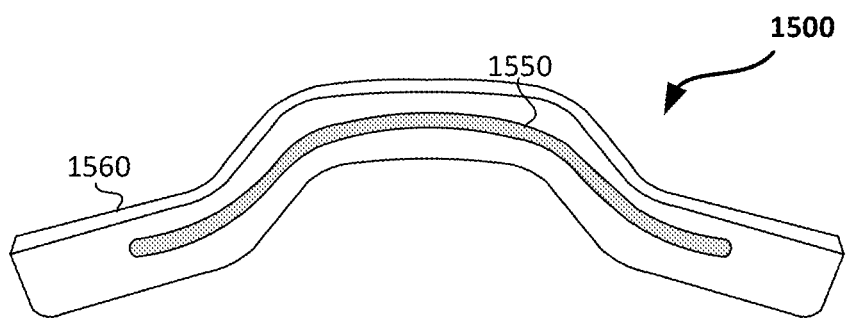
Figure 17A:
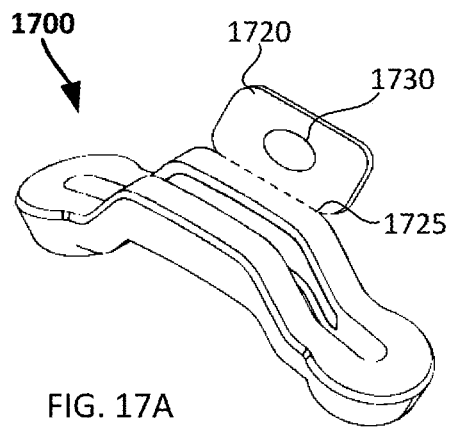
Figure 17B:
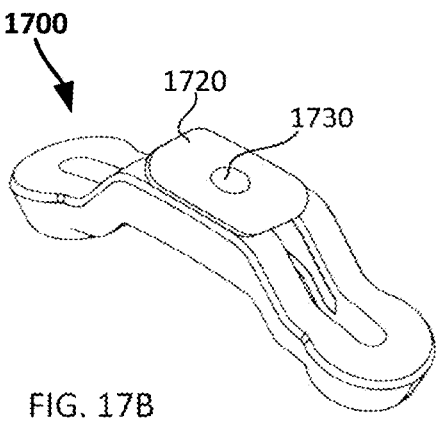
Figure 17C:
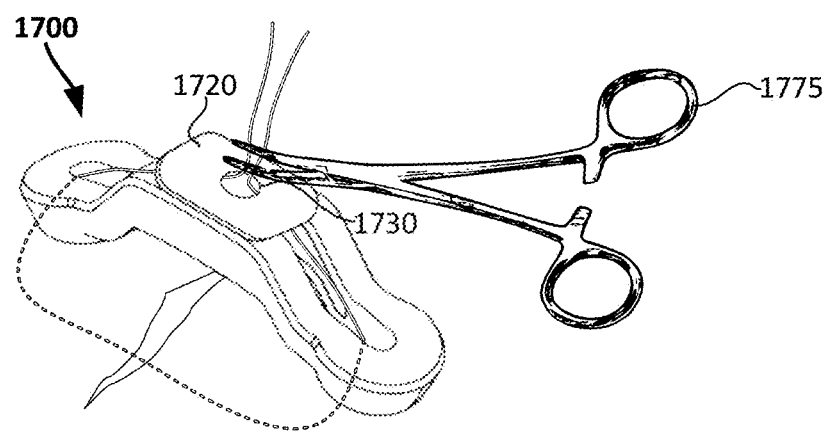
Figure 18A:
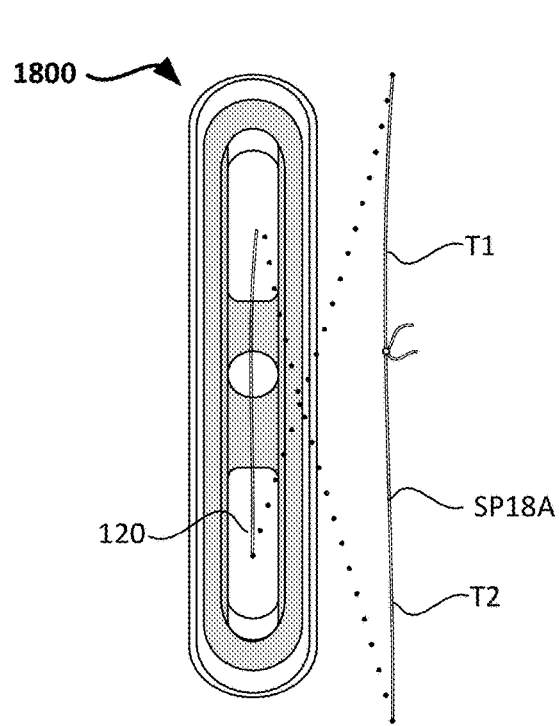
Figure 18B:
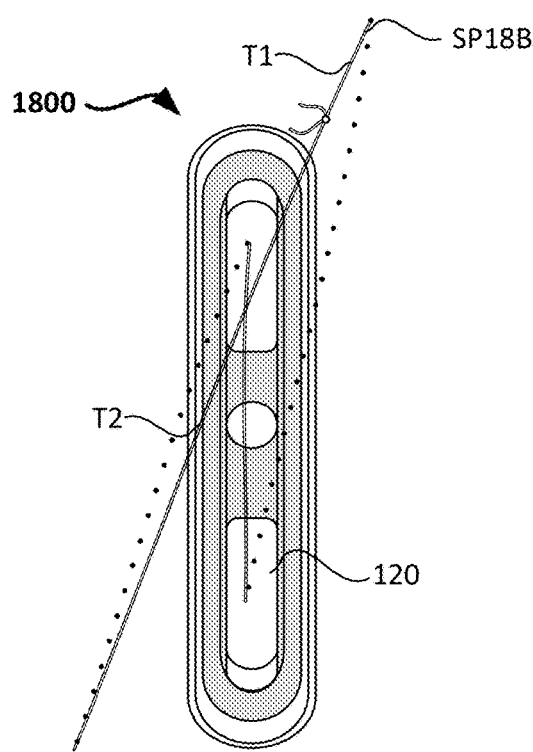
Figure 18C:
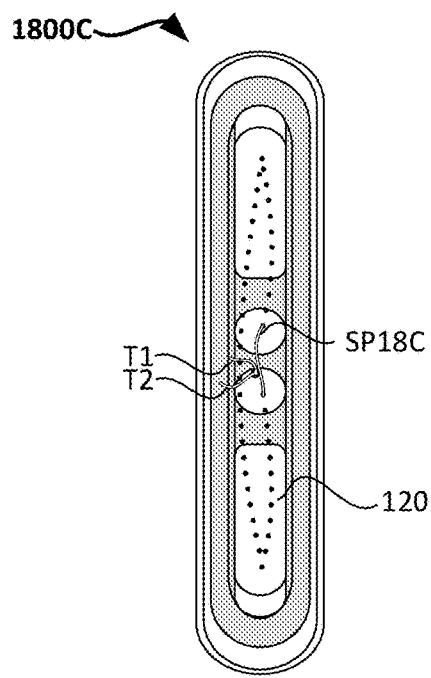
Figure 18D:
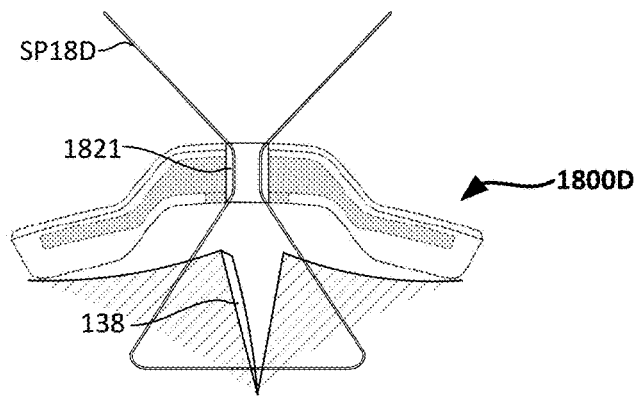
Figure 18E:
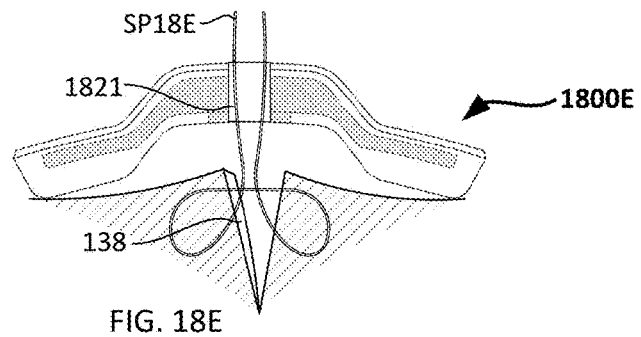
Figure 18F:
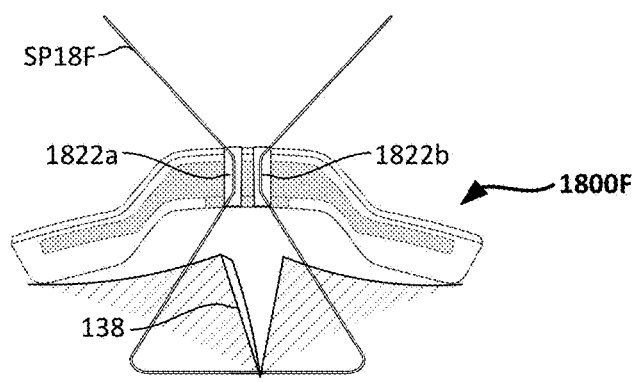
Figure 18G:
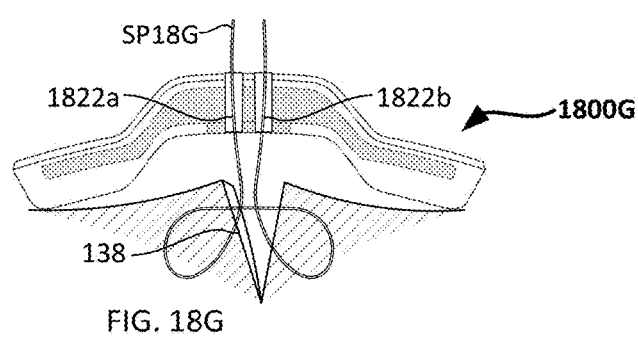
Figure 19:
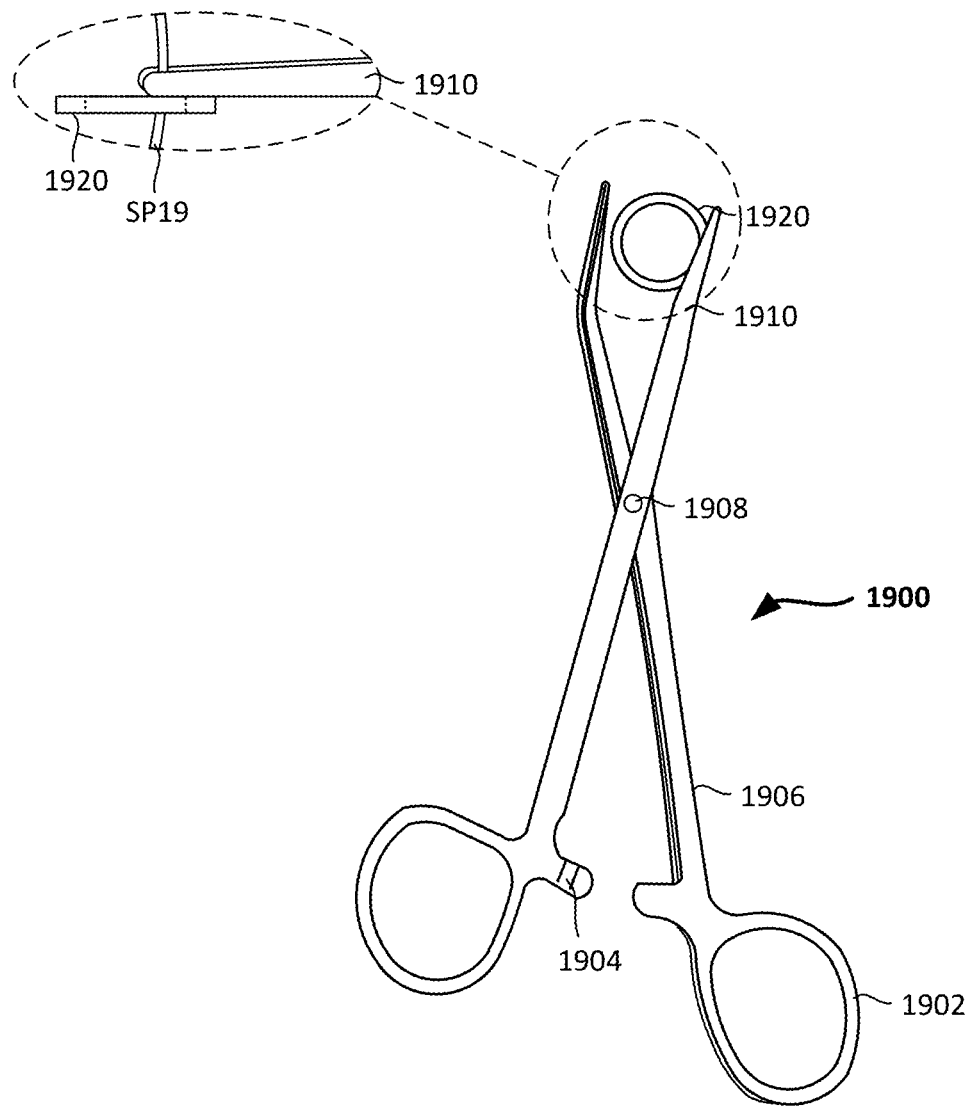

FIGS. 5A-B are a schematic side view and an associated graph showing the thickness of various bodies within the suture bridge of FIG. 1;

FIGS. 6A-G are schematic right, left, bottom, top, front, back and perspective views of one example of a suture bridge;

FIGS. 7A-G are schematic illustrations of top, side, bottom, front, cross-sectional and perspective views of an insert;

FIGS. 8A-G are schematic illustrations of top, side, bottom, front, cross-sectional and perspective views of a shell;

FIGS. 9A-B are schematic side views of a suture bridge being uses to close a wound with first and second suture patterns;

FIGS. 10A-B are photographs showing cheesewiring that may result from conventional techniques;

FIG. 11 is a schematic showing one variant of a suture bridge leg, the leg having a rounded bottom;

FIGS. 12A-D are schematic representations showing the shape of a suture bridge at different stages of use, and a detailed schematic view of the contact portion of a suture bridge;

FIGS. 13A-J are screenshots of various steps from an animation showing the use of the device to close a wound;

FIGS. 14A-B are schematic top views of an H-shaped suture bridge, and a similar H-shaped suture bridge having a flexible connecting member;

FIG. 14C is a schematic top view of a three-member suture bridge;

FIG. 14D is a schematic top view of an X-shaped suture bridge and one possible suture pattern;

FIGS. 15A-B are schematic top and side views of another variant of a suture bridge, the suture bridge having varying widths;

FIGS. 16A-C is schematic view of a kit that includes a suture bridge, a surgical needle, a suture and a retainer, and one possible suture pattern;

FIGS. 17A-C are schematic perspective views of a suture bridge having an integrated pressure relief member in the open and closed conditions, and one possible suture pattern;

FIGS. 18A-C are schematic bird's eye views of two suture patterns having pulleys, and a third bird's eye view of a suture pattern on a bridge having two central eyelets;

FIGS. 18D-G are schematic cross-sectional views of various suture patterns; and FIG. 19 is a schematic perspective view of a clamp having an integrated retainer.

Various embodiments of the present invention will now be described with reference to the appended drawings. It is to be appreciated that these drawings depict only some embodiments of the invention and are therefore not to be considered limiting of its scope.

DETAILED DESCRIPTION

Despite the various improvements that have been made to wound closure devices, conventional methods suffer from some shortcomings as discussed above.

There therefore is a need for further improvements to the devices and methods used to help facilitate proper and quicker healing of a wound. Among other advantages, the present disclosure may address one or more of these needs.

The disclosed suture bridges will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

These and other advantages will become more fully apparent to one of skill in the art upon consideration and review of this disclosure. While this disclosure describes various detailed embodiments, it is not intended to be limited to only the illustrated and described embodiments. The disclosed embodiments may be varied, modified, and altered without departing from the scope of the inventions described herein. Further, while many variations are contemplated for different applications and design considerations, for the sake of brevity each and every contemplated variation is not individually described.

The suture securing devices, systems, and methods described herein may be used to secure a suture and reduce or eliminate the likelihood that a suture may become inflamed, infected, ingrown, and/or reopened and increase the length of time that the suture can remain in place, among other purposes. Additionally, the devices disclosed herein may be capable of allowing a physician to apply a large force when tying a suture without damaging nearby tissue, and in some cases may be used to avoid the usage of skin grafts or flaps to close relatively large wounds.

FIGS. 10A-B are photographs showing a wound that is sutured together via a conventional technique (FIG. 10A), and the resulting cheesewiring that may occur from such techniques (FIG. 10B). Specifically, FIG. 10A shows a wound disposed between two portions of skin, and tied together via a suture. FIG. 10B shows the same after thirty minutes, after the suture has been removed. As shown, high tension in suture has caused the suture to damage some of the soft tissue ("cheesewiring"). To address this problem, solutions have been proposed which include reengineering the materials and configurations of the suture itself. Additionally, in certain clinical applications, it may be desirable to apply greater tension than usual on the suture, for example, to avoid the need for a skin graft. In such examples, high tension on the suture may result in lacerations and tearing of the skin. The present suture bridges may allow for high-tension closure of wounds while protecting the patient's tissue.

With reference to FIGS. 1-6, a first example of a suture bridge, suture bridge 100, will now be described. Suture bridge 100 includes a first leg 106, a second leg 108, a first support 110, a second support 112, a traversing member 114, and a spacing, often referred to as a "wound eversion void" or "void" 132 disposed below the traversing member. A ridge 128 is formed in at least portions of the traversing member, the supports, and the legs and this will be described in greater detail below. Suture bridge 100 also includes a bottom surface 102 and a top surface 104 opposite of bottom surface 102. Suture bridge 100 functions to extend the useful life of sutures and to reduce damage to skin while being employed by the most common suture patterns.

At ends opposite first leg 106 and second leg 108, first support 110 and second support 112 are connected together by traversing member 114 at obtuse angles. Together, first leg 106, second leg 108, first support 110, second support 112, and traversing member 114 define a bridge structure. Traversing member 114 is located in between first leg 106 and second leg 108 and is elevated away from first leg 106 and second leg 108 by first support 110 and second support 112 to form an elevated wound eversion void 132.

Wound eversion void 132 is formed beneath traversing member 114 and is configured to accept an everting wound 138. Similar to first support 110 and second support 112, traversing member 114 may be thicker, as measured from top surface 104 to bottom surface 102, than first leg 106 and second leg 108. The added thickness of traversing member 114, along with first support 110 and second support 112, provide a greater stiffness for suture bridge 100 in its elevated portion. The increased stiffness helps withstand forces of different suture patterns and helps resist suture bridge 100 collapsing or bending at wound eversion void 132. In alternate embodiments, first support 110, second support 112 and traversing member 114 increase stiffness by incorporating alternate or additional materials, in addition to or instead of adjusting the overall thickness of the device. Thus, a suture bridge may be formed having a relatively constant thickness but different stiffness and deformation characteristics along its length.

As can be seen in FIGS. 1-4, traversing member 114 is elevated away from a patient's skin 136 and wound 138. Traversing member being elevated and rigid helps facilitate wound eversion into wound eversion void 132 as wound 138 is pressed together by suture bridge 100 and the accompanying suture. When suture bridge 100 is used with a suture on a wound, wound eversion void 132 is positioned generally above the wound to facilitate wound eversion. Wound 138 may or may not contact bottom surface 102 in wound eversion void 132.

First leg 106 and first support 110 connect to form an obtuse angle at inflection point 116. Likewise, second leg 108 and second support 112 connect to form an obtuse angle at inflection point 118. Inflection points 116 and 118 cradle and trap sutures, for example, horizontal mattress sutures, that apply a downward and inward force on suture bridge 100. In some examples, inflection points 116 and 118 form defined angles to entrap and restrict movement of the suture. Inflection points 116 and 118 help enable common suture patterns, like a horizontal mattress suture, to be used with suture bridge 100.

Ridge 128 is located on top surface 104 of suture bridge 100 primarily along the length of traversing member 114. In some examples the ridge extends down the length of the first support and the second support 112. Ridge 128 may provide added strength, rigidity, and stiffness to suture bridge 100 to help withstand inward and downward forces applied by a suture.

Suture bridge 100 addresses many of the shortcomings existing with current suture techniques and devices. For example, suture bridge 100 extends the useful life of sutures. By elevating the sutures away from a patient's skin, the suture may last longer without causing irritation to the skin. Additionally, because pressure from the suture is reduced and more evenly spread across the surface of a patient's skin, a suture can stay in longer, allowing a wound more time to heal while avoiding conditions such as necrosis of the skin. In at least some examples, suture bridge 100 is approximately 33.75 mm in length and 8.15 mm at its greatest width. Alternatively, a larger suture bridge 100 may formed in the same proportions described herein, the suture bridge being approximately 10.35 cm in length by 2.5 cm in width. In one example, the length of the suture bridge may be formed in a length of between 1.0 cm and 15 cm, and the width may be adjusted accordingly. It will be understood that all of the other elements of the suture bridge (e.g., legs, traversing member, supports and slots) may be scaled accordingly.

Suture bridge 100 may also be used in conjunction with many common types of suture patterns, including a simple interrupted suture, buried dermal suture, pulley ("far-near-near-far") suture, horizontal mattress suture, and a vertical mattress suture. Suture bridge 100 is sturdy and rigid enough to not collapse under the forces of any common type of suture while still gathering the wound, encouraging wound eversion and proper healing of the wound.

As can be seen in FIGS. 1-6, suture bridge 100 includes at least two legs, where first leg 106 and second leg 108 are located at opposite ends of the bridge. Located on bottom surface 102 of suture bridge 100 at first leg 106 and second leg 108 are patient contacting surfaces 126. Patient contacting surfaces 126 reduce the overall pressure on a patient's skin 136 that would normally occur without suture bridge 100, allowing for longer use of the suture. In alternate embodiments, there may be multiple legs and multiple patient contacting surfaces. In at least some variants, legs 106, 108 are curved at the terminal ends as shown in FIG. 11. Specifically, the patient contacting surfaces 126 may themselves be rounded and the distalmost portion 127 of the leg 126 may curve away from the patient's body.

First leg 106 and second leg 108 are of a sufficient thickness to be sturdy, yet still flexible. In some examples, the two legs are symmetric, formed of the same materials in the same configuration and behave in the same or in similar manners. Alternatively, a different and more flexible material could be used for the first leg and the second leg to allow for different degrees of flexibility in each of the legs.

The flexibility of first leg 106 and second leg 108 allows them to contort and adapt to a patient's skin 136 as the patient moves. The legs are flexible to reduce skin irritation and pressure necrosis and allow movement of the patient's skin. Additionally, the flexibility of first leg 106 and second leg 108 provides for better patient comfort and reduces annoyances, such as suture bridge 100 catching on articles of clothing.

Figure 2A:
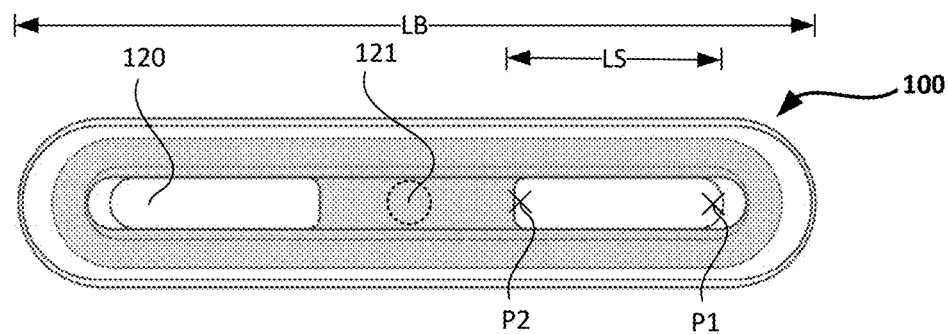
FIG. 2A is a schematic top view of the suture bridge of FIG. 1.
Figure 2B:
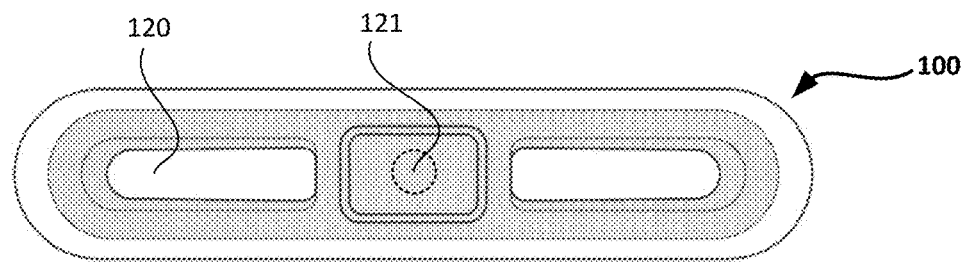
FIG. 2B is a schematic bottom view of the suture bridge of FIG. 1.

As shown in FIGS. 2A-B, first leg 106 and second leg 108 each contain an elongated slot 120. Slots 120 on first leg 106 and second leg 108 extend fully through suture bridge 100 from top surface 104 to bottom surface 102. Slots 120 can be used with a simple interrupted suture to secure suture bridge 100 to a patient over a wound 138 to extend the life of the suture and to encourage proper healing of the wound. As shown, slots 120 have a length and a width, the length of the slots being chosen to allow travel of the suture when gathering tissue to form the wound eversion as described above. In at least some example, the length, "LS", of the slots 120 will determine how much wound eversion is permitted. Specifically, slots 120 may have length "LS" that is approximately 15%, 20%, 25%, 30% or 40% of the overall length "LB" of the suture bridge. Alternatively, because the tissue being pulled together will also be gathered into the wound eversion void and up toward the traversing member, slots 120 may be proportional to the height of the wound eversion void 132 (e.g., 1.2×, 1.25×, 1.3×, or 1.5× the height of the wound eversion void).

When using the slots 120, even the inexperienced operator can achieve maximal eversion closure by placing the suture at the outermost space within the slot (e.g., at a point farthest away from the traversing member within slot 120 such as point P1 in FIG. 2A). As tension is placed on the suture, tissue is gathered and the suture will travel within the slot inwardly toward the traversing member (e.g., travel closer to point P2 in FIG. 2A, and bringing with it the coupled tissue), allowing for eversion of the wound within the wound eversion void 132 below the traversing member 114.

In alternate embodiments, slots 120 may be configured as circular holes in first leg 106 and second leg 108. In some examples, instead of elongated slots on each leg 106, 108, one, two, three or more circular or oval apertures may be provided on each leg. In at least some examples, slots 120 on opposing legs may be spaced from one another by approximately 8.05 mm. In at least some examples, the distance between the slots may be between 4 mm and 15 mm. Additionally, each slot may be between 2 and 3 mm in width and between 4 and 30 mm in length.

Optionally, and as shown in phantom lines only in FIGS. 2A-B for the sake of clarity, a central aperture 121 may be formed in the center of the traversing member 114 and define a passage from the top to the bottom of the device. Central aperture 121 may be substantially circular, or oval, and may be equidistant from slots 120. In examples having central aperture 121, the physician may thread a suture through this passage according to his need. Suture patterns utilizing this central aperture will best be shown near the end of this disclosure with reference to FIGS. 9A and 9B. In embodiments having both a central aperture 121 and slots 120, the physician may thus select the most desirable suture configuration. For example, to obtain maximal wound eversion, slots 120 may be used to allow the suture to travel therethrough when gathering tissue to evert it. Alternatively, if wound eversion is not a priority, central aperture may sufficiently accomplish the task of closing the wound.

Figure 3:
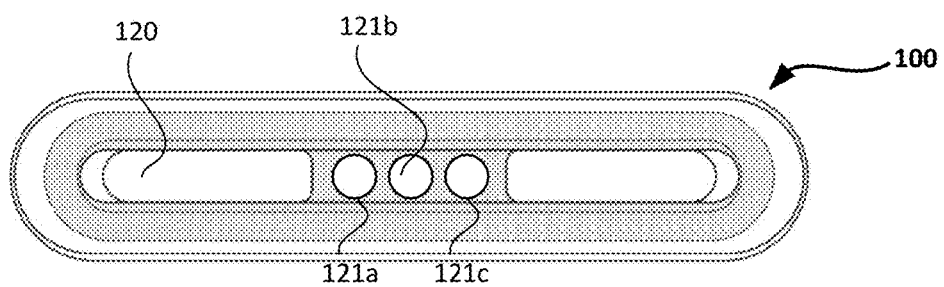
FIG. 3 is a schematic top view of another embodiment of a suture bridge having multiple central apertures.
Figure 4:
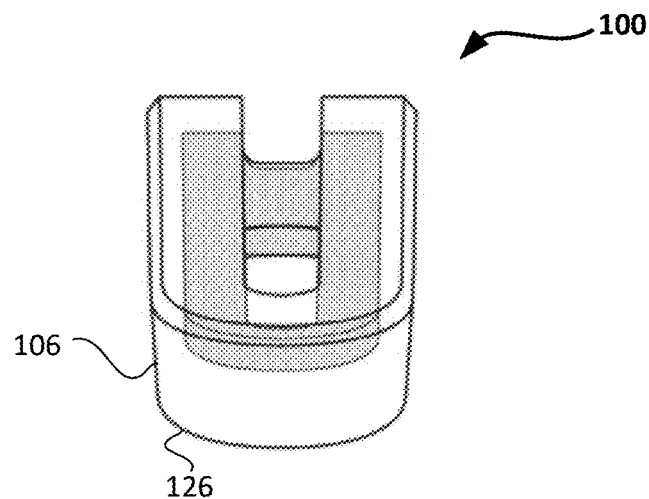
FIG. 4 is a schematic front view of the suture bridge of FIG. 1.

As shown in FIG. 3, a suture bridge 100 may instead include multiple central apertures 121a-c in the traversing member. Thus, the traversing member may have no central apertures, a single central aperture, or multiple (e.g., two, three, four or more) central apertures. It will be understood that the shape and/or size of the central apertures may be the same or different from others.

First leg 106 is connected to a first support 110, and second leg 108 is connected to a second support 112. First support 110 and second support 112 rise up and slope inwardly at an angle a1 of between 0 and 60 degrees with respect to first leg 106 and second leg 108 (See FIG. 5A). More specifically, in some examples, the angle a1 may be between 30 and 60 degrees, which allows for a raised traversing member for maximal wound eversion. Alternatively, the angle a1 may be between 0 and 30, such an angle allowing the traversing member to be closer to the wound, which results in smaller forces between the legs and the patient's skin. Such an embodiment may be useful for high-tension wound closure in clinical settings such as when a skin graft is avoidable. For example, it is believed that with an angle a1 of between 30 and 60 degrees, it may be possible to apply a force of between 4 and 50 Newtons, which is an amount that may injure the adjacent tissue if applied via a suture only without the suture bridge. In at least some examples, the angle is selected so that a force of at least 25 Newtons may be applied to a suture without damaging the tissue. Additionally, it will be appreciated that raising the traversing member away from the wound may result in greater pressure on the tissue below the legs so that other components are used to alleviate this pressure as will be discussed shortly. In at least some examples, the angle a1 may be closer to 0 degrees (e.g., between 0 degrees and 30 degrees) and the traversing member is either completely aligned with the legs, or slightly raised by a distance of between 0 and 10 mm from the wound underneath.

In some examples, first support 110 and second support 112 may be thicker, as measured from top surface 104 to bottom surface 102, than first leg 106 and second leg 108. The thickness of first support 110 and second support 112 increase the stiffness of first support 110 and second support 112 as compared to first leg 106 and second leg 108. In alternate embodiments, first support 110 and second support 112 are of roughly the same thickness as the legs but incorporate different materials. These materials may be incorporated by creating first support 110 and second support 112 entirely from different materials, or alternatively they may have an internal or external support structures as will be described in greater detail with references to FIGS. 7-8.

In some embodiments of the suture bridge, the entire suture bridge or a portion, for example, the bottom surface 102 may include a coating of additional medications. In these embodiments, a coating of one or a combination of growth factors, antimicrobials, or other agents for transfer to a patient's skin and wound to assist in proper healing of the wound. Alternatively, in some embodiments, the suture bridge may entirely or partially be impregnated with one or more additional medications to assist in proper healing of the wound.

Suture bridge 100 may be formed partially or entirely from any sturdy and resilient material, such as silicone, thermoplastic polyurethanes (TPU), rubber, metal, plastic, polypropylene, polyethylene, acrylonitrile butadiene styrene (ABS), high impact polystyrene (HIPS), poly vinyl chloride (PVC) polycarbonate, thermoplastic elastomers, polybutylene terephthalate, ethylene vinyl acetate, nylon a low-density polyethylene, linear low-density polyethylene, and suitable combinations thereof. The suture bridge may also be made of one material of varying thickness, or by using a spine or ridge, to provide support for the traversing member while remaining flexible at the first leg and the second leg.

Alternatively, the suture bridge may be formed of multiple portions that are coupled together, the inner and outer portions including different materials to provide support and strength for the traversing member while remaining flexible at the first leg and the second leg. For example, any number of bodies may be used to form the suture bridge entirely, the support structures, and the legs, such bodies being formed of different material and being configured to house or otherwise couple to one another. One example of such a bridge is shown in FIGS. 6A-G having two components. Examples of these components will be described in more detail below.

In the example shown, suture bridge includes an inner portion or insert 150 (FIGS. 7A-G) and an outer portion or shell 160 (FIGS. 8A-G), the insert 150 and the shell 160 being formed of different materials and collectively forming the bridge body that includes the legs, supports and traversing member. As shown in this example, shell 160 is co-molded over insert 150 so that it completely encompasses insert 150, encasing it on every side. Alternatively, shell 160 may only partially cover insert 150 so that the upper surface of insert 150 is not covered, for example, at the top of the device, but the bottom surface is covered to provide comfort to the patient.

Details of insert 150 will best be understood with reference to FIGS. 7A-G. Insert 150 may be formed of a material that is more rigid than shell 160. Insert 150 may extend between a first end 152 and a second end 154 and form a general bridge shape having slots 156 defined therethrough on opposing ends. It will be understood by looking at FIGS. 7A-G, for example, that insert 150 forms portions of the legs, supports and traversing member of suture bridge 100. Although not shown, insert 150 may also include one or more apertures in the traversing members as desired. The thicknesses of insert 150 "TI" will vary along its length as will be discussed in greater detail below. Sufficient to say at this point that the insert will be thickest at its center and thinnest near the first and second ends 152, 154. Additionally, it will be understood that multiple inserts may be provided within the body of the suture bridge instead of a single insert.

In some examples, the insert 150 may be overmolded with an elastomer, such as a silicone, and the material of the insert 150 may be selected from a heat tolerant material that is not likely to melt during the overmolding of the shell 160. For example, an insert 150 covered by silicone may require a hot mold, and the insert 150 may be tolerant to heat up to the temperature necessary for the hot mold. Suitable materials for the insert 150 may include any of those discussed above, or high temperature tolerant materials having a relatively high flexural modulus (e.g., 1.5-4 GPa), such as polyether ether ketone (PEEK) and polyetherimide (e.g., Ultem). Thus, in some examples, the insert 150 may be formed of Polyether ether ketone (PEEK), and shell 160 may be formed of a soft silicone.

Turning now to shell 160, the details of which will best be understood with reference to FIGS. 8A-G. Shell 160 may extend between a first end 162 and a second end 164 and have the same general bridge shape as insert 150 and suture bridge 100. Shell 160 may also include slots 166 defined therethrough on opposing ends, the slots 166 being shaped, sized and spaced to align with slots 156 of insert 150. Although not shown, shell 160 may also include one or more apertures in the traversing members to align with the apertures of the insert 150 so that a suture may be passed through the traversing member. In at least some examples, shell 160 is thickest at first and second ends 162, 164. For example, shell 160 may have a thickness "TS" of between 1.0 mm and 10 mm at the legs such thickness being capable of relieving pressure on the patient's skin when tension is applied to a suture. In at least some examples, shell 160 forms 60%, 70%, 75% or more of the total volume of the legs of the suture bridge. Additionally, as shown in FIGS. 8A-G, shell 160 forms bulbous, almost circular, curved contacting members 826 that are wider than the rest of the device. This feature is optional, and it will be understood that in other embodiments, the shell is substantially stadium-shaped when seen from above as illustrated in FIG. 2A.

In at least some examples, the insert 150 and the shell 160 are first co-molded, and the slots are simultaneously formed through the two members after the molding process. It will be understood by looking at FIGS. 8A-G, for example, that shell 160 forms portions of the legs, supports and traversing member of suture bridge 100. The thicknesses of shell 160 "TS" will vary along its length as will be discussed in greater detail below, and in some cases this thickness will vary according to a mathematical relationship with the thickness of the insert 150.

Shell 160 may be selected from a relatively soft material that allows for dissipation of pressure and that can be molded without sharp edges to prevent damage or laceration of the skin. The softness or hardness of the material for the shell may be measured with Shore scales. For example, hard plastics are typically measured on the Shore D scale. Softer materials on the Shore A and A00 scales may be used. In some examples, the shell may be formed of a silicone with Shore A hardness of 40 or less. In at least some examples, the shell may be formed with a material having a Shore A hardness of 60 or less. In at least some example, the material should have a Shore A hardness of equal to or less than 60 or a Shore A00 hardness of equal to or less than 90. In some examples, shell 160 is formed by overmolding a biocompatible material chosen from ones that are easily sterilized via steam or an autoclave, such as soft silicone overmolded over the insert 150.

In some other examples, a biocompatible thermoplastic elastomer (TPE) or biocompatible thermoplastic urethane (TPU), or combinations thereof may be used for the shell. In such examples, the materials of the insert may not necessarily need to be a high tolerant material, and the insert may be formed of such materials as common types of plastics, nylon, polypropylene, polyoxymethylene (e.g. Delrin or Acetal), Acrylonitrile butadiene styrene (ABS), and the like. Thus, devices having a Delrin insert and a TPU shell may be used.

In some examples, the device 100 has a substantially equal total thickness in the traversing member 114 as the legs 106, the thicknesses being measured from the top surface to the bottom surface (i.e., T114=T106 as shown in FIG. 5A). Though these thicknesses are equal, the portions of the thicknesses attributable to the insert and the shell may be different. For example, at thickness T114 near the traversing member, the shell may form a minority of the thickness, for example, between 10% and 50% of the thickness, while the insert forms the remaining portion of the thickness (e.g., 50% to 90% of the thickness). Conversely, at thickness T106 near the legs, the shell may form a majority of the thickness, for example, between 50% and 90% of the thickness, while the insert forms the remaining portion of the thickness.

FIG. 5B will be understood in conjunction with FIG. 5A above it, and shows the thicknesses of the shell (and implicitly the insert) at certain points along the length of the suture bridge shown directly above it and aligned therewith. As shown in FIG. 5B, possible ranges of the percentage of the bridge body thickness attributable to the shell may vary along the length of the body from one end to the other. To better understand FIG. 5B, three vertical lines are shown with labels "T1", "T2" and "T3". "T1" shows possible thicknesses at point "T1" along the traversing member so that it will be understood by looking at the corresponding shaded region that the shell may form between 10% and 50% of the total thickness of the bridge at this location. "T2" shows possible thicknesses at point "T2" along the leg so that it will be understood by looking at the corresponding shaded region that the shell may form between 50% and 90% of the total thickness of the bridge at this location. "T3" shows possible thicknesses at point "T3" along the leg so that it will be understood by looking at the corresponding shaded region that the shell may form 100% of the total thickness of the bridge at this location. Thus, the graph shows some possible configurations in which the shell forms a percentage of the bridge body, the shaded region showing certain possible makeups of the shell within the bridge body. At extremes of the bridge body, the shell makes up 100% of the thickness of the bridge body (e.g., in one example, the insert does not extend to the outermost portion of the leg). The shell percentage decreases and increases along the body as desired to obtain a bridge body having the preferred deflection and deformation properties.

It will be understood that the percentage thickness of the insert will simply be equal to 100% minus the percentage thickness of the shell, so that a shell thickness of 40% equates to an insert thickness of 60%. Specific thickness ratios of shell: insert may depend on the stiffness of the materials selected.

In at least some examples, the shell is thickest adjacent the legs of the device, and thinnest adjacent the traversing member. Conversely, the rigid insert may be thickest adjacent the traversing member, and thinnest adjacent the legs. It will be understood that the suture bridge thicknesses may vary with materials. For example, a less stiff insert, such as polypropylene, may be used instead of PEEK, but the central portion may need to be thicker to compensate for the lack of stiffness of the material.

By varying the thicknesses of insert 150 and shell 160 in this manner, the deformation characteristics of the device 100 may be carefully chosen. In the example shown in FIGS. 7-8, the increased thickness of the deformable shell 160 may help relieve some of the pressure of the device at the legs of the bridge, while the increased thickness of the rigid insert 150 at the traversing member may provide strength, rigidity, and stiffness to suture bridge 100 to help withstand inward and downward forces applied by a suture.

With reference to FIGS. 9A and 9B, two examples of using the suture bridge are shown. In FIG. 9A, the physician has opted to use central aperture 121 instead of the slots 120 for this specific application, and the suture "S1" generally pierces through two portions of the skin on either side of the wound and the two tails of the suture extend vertically away from the skin through the central aperture 121. Conversely, in FIG. 9B, the physician has elected to use the slots 120 instead of the central aperture, passing the suture "S2" through the two portions of the skin on either side of the wound, and passing each tail of the suture through one of the slots on either side of the central aperture.

At least portions of the suture bridges of the instant disclosure may be flexible and have spring-like properties. FIGS. 12A-D illustrates one example of a suture bridge according to the present disclosure during use. For the sake of simplicity, the suture bridge 1200 is shown as a single component, although it will be understood that suture bridges having both an insert and a shell are contemplated and that the instant description applies to both unitary and multi-component bridges.

Figure 12A:
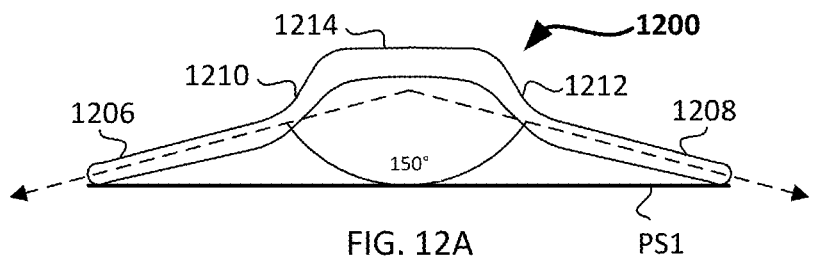

FIG. 12A illustrates suture bridge 1200 in a rest ("or resting") condition on a patient surface "PS1" (i.e., with no external force applied thereto), the suture bridge having a pair of legs 1206, 1208, a pair of supports 1210, 1212 and a traversing member 1214 extending between the two supports. The patient surface may be, for example, the patient's skin at the site of a wound. As shown, the legs 1206, 1208 may form a leg resting angle defined as the angle between the two legs of the bridge, of, for example, approximately 150 degrees when the suture bridge is at rest, the legs and supports serving to elevate the traversing member away from patient surface PS1.

Figure 12B:
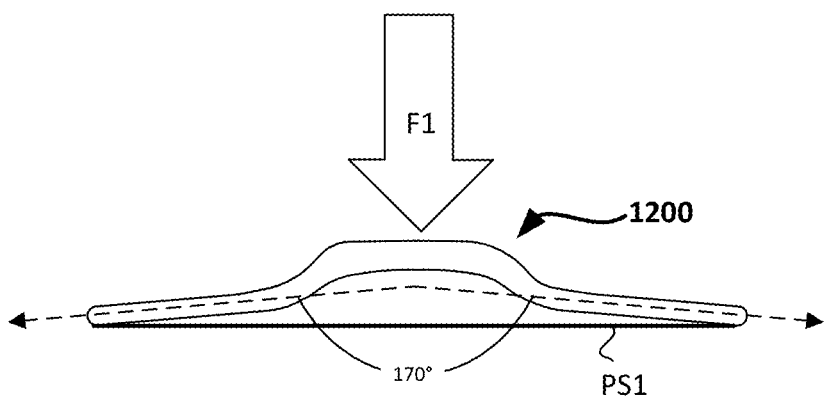

As shown in FIG. 12B, an external force "F1" may be applied to a portion of the suture bridge 1200, such as the traversing member 1214. In at least some examples, this external force "F1" may be a force applied by the tightening of a suture. The external force "F1" may flatten the suture bridge 1200 so that the angle between the legs increases to 170 degrees. Note in FIG. 12B, that the traversing member 1214 is closer to patient surface "PS1" when the external force is applied than at rest. In this flattened condition, the physician may begin to couple the suture bridge to the wound via a suture using any of the techniques described above.

Figure 12C:
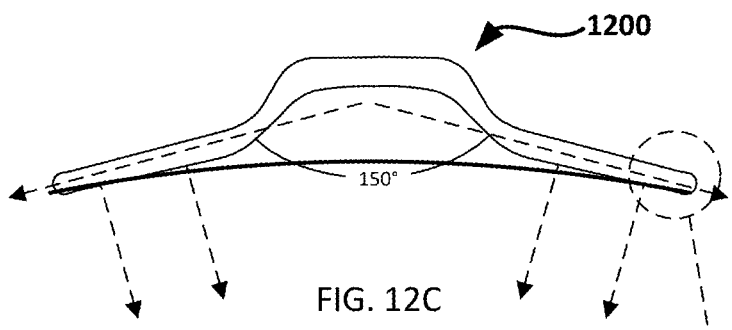
Figure 12D:
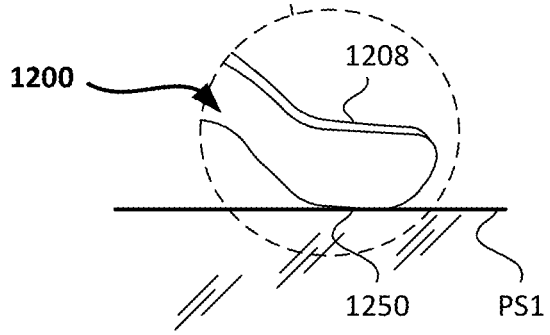

At least portions of suture bridge 1200 may be formed of a material that returns to its original condition after the external force "F1" has been removed. Thus, the suture bridge 1200 may act as a spring and may have a memory to return to its resting condition absent any external force. Specifically, when external force "F1" is removed, suture bridge may return to the same or a similar condition shown in FIG. 12A. Because the bridge is coupled to the patient's skin, the returning of the suture bridge 1200 to its rest condition, will gather patient surface "PS1" and pull it up to the cavity underneath the traversing member (FIG. 12C). There are at least two advantages to this technique. First, gathering of the patient's skin in this manner results in wound eversion, which is believed to provide at least some of the benefits previously discussed. Additionally, deep dermal and superficial subcutaneous tissue apposition is possible from the inward compressive forces, which partially compress the device. Additionally, wounds may be closed under very high tension without apparent damage to the tissue. This is believed to be the result of both the angle of the suture coming out of the skin and from the increased surface area of the device when compared with the same suture performed without the device.

Additionally, without being bound by any particular theory, it is believed that the degrees to which the suture bridge springs back to its resting condition when an external force is removed is related to the hardness (i.e., durometer) of the material of either the shell or the insert. In at least some examples, the shell of the suture bridge has a lower hardness than the insert. In at least some examples, the shell includes an elastomer having a Shore A durometer of 80-90 or a Shore A durometer of 30.

To illustrate the memory of the device, a suture bridge was formed having legs and a leg resting angle of 150.55 degrees. A compressive force "F1" of 16.5N was applied to the suture bridge for 45 minutes. When the compressive force "F1" was relieved, the suture bridge returned to a leg angle of 153 degrees. In a clinical setting, this rebound would occur after suturing, and after the external force is removed, and would gather the tissue with it.

In addition to the memory properties of the suture bridge, additional features may be included to improve the gathering of the patient's skin. For example, as shown in the detailed view of FIG. 12D, suture bridge 1200 includes a leg 1208 having a skin-contacting portion 1250. Skin-contacting portion 1250 may be formed as part of the shell. Additionally, in at least some examples, skin-contacting portions 1250 on each leg may include a "tacky" material or a rough surface with a rough topography that provides a prerequisite coefficient of friction with the patient surface "PS1" so that the skin-contacting portions aid in the gathering of the tissue. In at least some examples, the coefficient of friction of the skin-contacting portions will be chosen based on the intended application. In at least some examples, the coefficient of friction is between 0.38 to 0.5 or from 0.5 to 1.

Figure 13A:
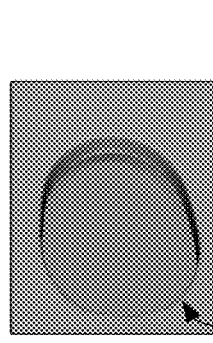
Figure 13B:
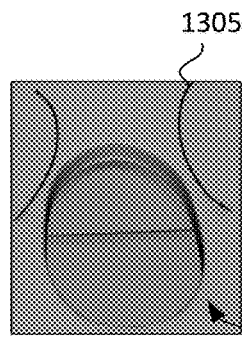
Figure 13C:
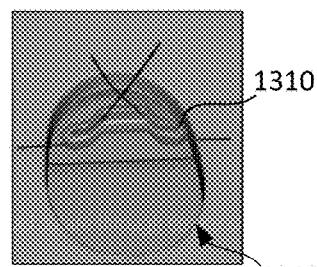
Figure 13D:
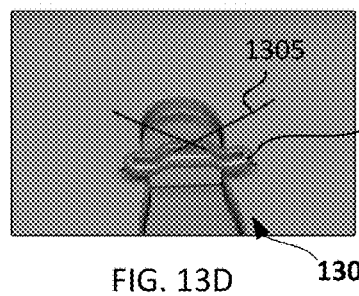
Figure 13E:
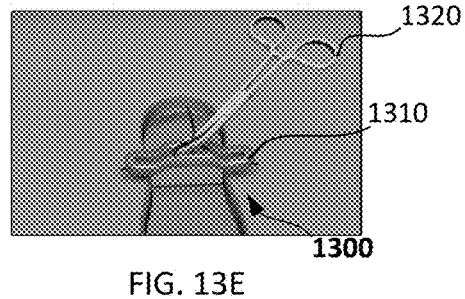
Figure 13F:
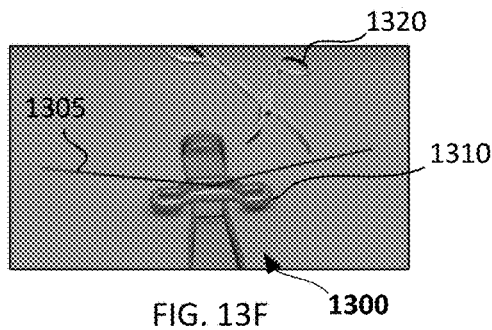
Figure 13G:
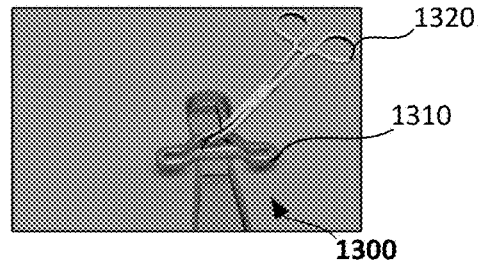
Figure 13H:
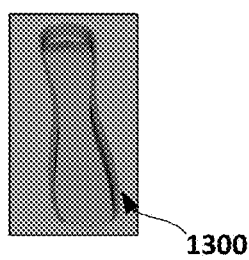
Figure 13I:
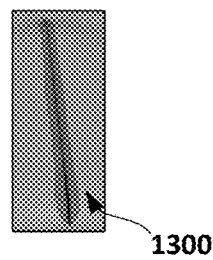
Figure 13J:
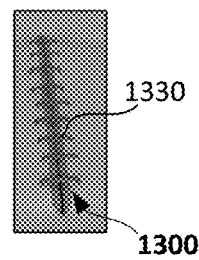

In use, any of the suture bridges described herein may help close a wound. Turning to FIGS. 13A-J, a series of screenshots from an animation is presented which show the use of the device. The suture bridges may be used to aid in the closure of a large wound 1300 formed after Mohs surgery. The wound 1300 may begin as a relatively large wound, in this example, shown as being substantially oval. To close the wound, a surgeon may first perform a large bite procedure with the needle and suture 1305, passing the suture on either side of the wound approximately 1 cm from the skin edge without undermining using 2-0 or larger nylon suture (FIG. 13B). The physician may then place the suture bridge 1310 in the resting condition across the wound with the legs of the suture bridge being disposed on either side of the wound, the traversing member being disposed directly above the wound, and the longitudinal axis of the bridge being substantially perpendicular to the wound. The ends or tails of the suture 1305 may be brought together and then inserted through the slots of the suture bridge 1310, the ends of the suture then crossing over the traversing member (FIG. 13C). An appropriate tension may be applied, for example, via a clamp 1320 to secure the suture, this tension causing the suture bridge to flatten, increasing the angle between the legs, the traversing member now being closer to the wound than in the resting condition (FIG. 13D). At this point, once the clamp 1320 is secured the suture bridge 1310 will continue to exert pressure on the wound 1300 to stretch the skin and the clamp may be used to hold the suture for approximately 5-10 minute intervals (FIG. 13E). The suture 1305 may be successively unclamped and retightened to allow for successive Mohs layers to be taken after the initial tightening. The tightening of the suture causes the wound to come together more easily after tissue expansion, and fully stretching may be achieved in approximately 30-60 minutes. Additionally, the suture bridge returns to its elevated resting condition, gathering and everting the wound and bringing it into the wound void and up toward the traversing member (FIGS. 13F-G). Finally, after an appropriate amount of time, the device can be removed (FIG. 13H), the wound being substantially smaller than it was originally (FIG. 13I). A linear closure may then be performed using staples, 1320, or sutures, adhesive or other suitable method (FIG. 13J). This technique may be used to minimize the presence and/or appearance of scars. Specifically, by using one of the suture bridges disclosed herein, the skin may be stretched allowing a closure under lower tension, the stretching of the skin helping to reduce the possibility of conspicuous scars. Thus, a method is contemplated of reducing scars using the steps outlined above, and scar revision surgery may also be possible using the bridges and techniques disclosed herein.

Other variations of the bridges are also possible as shown in FIGS. 14A-D. For example, FIG. 14A is a schematic top view of an H-shaped suture bridge 1400 that may be useful for larger wounds "W1". The H-shaped bridge 1400 is generally formed as two bridge members 1410, 1412, such as those shown in FIG. 1, joined together by a connecting member 1420. FIGS. 14A-15 show top views where the elevation of the bridge is not possible to see, although it will be understood that each bridge member in these figures may be formed similar to the bridges described above which include legs, support members, traversing member that are elevated from the wound. Additionally, each of the bridge members may include an insert and a shell as described above. Connecting member 1420 of FIG. 14A may include at least some of the materials used for the insert or at least some of the materials used for the shell, or a combination of them. In at least some examples, the H-shaped bridge includes a unitary shell that forms both shells of the bridge members 1410, 1412 and the connecting member 1420.

In some examples, the connecting member 1420 may be flexible so that the two bridge members 1410, 1420 may angle toward or away from each other as desired. As shown in FIG. 14B, bridge member 1412 is disposed at an angle of approximately 10 degrees with respect to bridge member 1410 so that the bridge members remain perpendicular to a curved wound "W2" at more than one location. In at least some examples, bridge members 1410, 1412 are parallel to one another, but are capable of flexing to form an angle of 1 to 60 degrees therebetween. Additionally, instead of an H-shaped suture bridge, variations such as a three-member bridge 1450 with three bridge members 1410, 1412, 1414 are also possible, each bridge member being connected by flexible or rigid connecting members 1420, 1422 as desired and disposed over wound "W3" (FIG. 14C). It will be understood that variations are also possible with four, five or more bridge members.

FIG. 14D is a schematic top view of an X-shaped suture bridge 1460, the bridge having two bridge members 1462, 1464 that are perpendicular to one another and intersect (or are joined together) at a central eyelet 1465. An X-shaped suture bridge 1460 may provide greater stability of a traversing member over the wound, and may provide flexibility to the physician in choosing an appropriate configuration or layout for the bridge and the suture pattern. It will be understood that this embodiment also contemplates raised traversing members so that central eyelet 1465 is elevated above the wound similar to that described above. One possible suture pattern SP14 is shown, although it will be understood that other suture patterns are possible including those that pass through the central eyelet 1465 of the X-shaped suture bridge.

FIGS. 15A-B are schematic top and side views of another variant of a suture bridge 1500. Suture bridge 1500 is similar to suture bridge 100 of FIG. 1 and may have both an insert 1550 and an outer shell 1560 forming a bridge body having a pair of legs, a pair of supports and a traversing member, and include some or any of the features of the previous embodiments. Suture bridge 1500 may also be formed using the material(s) discussed above in any of the configurations. Suture bridge 1500 is slightly different from other embodiments in that the insert 1550 has a substantially uniform thickness from one end of the insert to the other (i.e., portions of the insert adjacent the legs, the supports and the traversing member are made of a same thickness) (See, FIG. 15B). Instead, rigidity of insert 1550 is varied by changing its width. Specifically, as shown in the top view of FIG. 15A, insert 1550 has varying widths adjacent the legs, and steadily increases in width toward a midline of the insert, reaching a maximum width "WMAX" at the traversing member. Thus, even though the insert has a constant thickness (FIG. 15B), it also may have a greatest rigidity at the traversing member and a decreasing rigidity along its length as it approaches the legs. Shell 1560 may also have varying widths to properly house the insert therein, the shell's width being tailored to match that of the insert.

Any of the suture bridges described above may be provided as part of a kit 1600 as shown in FIG. 16A. Kit 1600 include any of the suture bridges described herein, such as suture bridge 1610 having an insert and a shell (the insert not shown in FIG. 16A), a retainer member 1620 in the form of a washer, a surgical needle 1630, and a strand of suture 1640 coupled to the needle. In at least some examples, a hybrid suture 1650 having flat portions 1652 that transition to round portions 1654 may be provided instead of a traditional suture 1640. Hybrid sutures such as these are available through TELEFLEX MEDICAL™ under the mark FORCE FIBER FUSION™. In at least some examples, the flat portions of such as suture will be disposed adjacent the skin, and aligning parallel to the incision margins while the round portions will be disposed adjacent the traversing member.

A number of suture patterns may be used in connection with the kit of FIG. 17A such as, for example, a simple interrupted suture pattern. FIG. 16B shows one possible suture pattern SP16 for use with the kit. As shown, a suture retainer member 1620 is placed on top of suture bridge 1600. Suture pattern SP16 passes through the slots of the suture bridge and are threaded through an aperture 1622 of the retainer (e.g., washer). In this embodiment, retainer 1620 serves to keep the suture tails together and in place above the suture bridge so that a clamp 1675 (FIG. 16C) can be used to easily grasp the suture tails.

FIGS. 17A-C are schematic perspective views of a suture bridge 1700 similar to that described above but having an integrated retainer member 1720. For the sake of clarity, the insert is not shown in this figure. Suture bridge 1700 may include a retainer member 1720 in the form of a substantially rectangular flap attached to the traversing member at one edge via a living hinge 1725. Living hinge 1725 may include a scored or thinned portion that allows the flap to open (FIG. 17A) and close (FIG. 17B). Additionally, retainer member 1720 may include an eyelet 1730 as shown. By having an integrated retainer member 1720, a separate washer may be eliminated from the kit. As shown in FIG. 17C, a simple suture pattern SP17 is shown in connection with the bridge 1700. The tails of the suture may pass through the eyelet 1730 of retainer member 1720. With the integrated retainer in the closed position, the tails of the suture are gathered together and it is easier to grasp both tails of the suture with a clamp 1775. Because the method may include several iterations of tightening and releasing the suture tails, the integrated retainer may make it easier to locate and grasp the suture tails quickly.

Two additional suture patterns are shown in FIGS. 18A-B, the two suture patterns utilizing "pulley" mechanisms. The bridges are disposed directly above a wound (not shown for clarity) substantially perpendicular thereto. In the suture patterns below, a solid line indicates a portion of the pattern that is disposed above the skin and visible to the physician, and dotted line indicates a portion of the suture pattern that is below the skin's surface. As shown in FIG. 18A, a first cis-pulley suture pattern SP18A includes a suture pattern that forms two substantially vertical sections (i.e., aligned with the longitudinal axis of the bridge), one between the two slots, and the other coupling the two suture tails T1, T2, and an X-shaped arrangement under the patient's skin. Alternatively, a trans-pulley suture pattern SP18B may be used, which includes a vertical section formed between the two slots and a diagonal formed from the coupling of the two suture tails.

FIG. 18C shows another bird's eye view of a suture bridge 1800C having two central eyelets and a simple pattern SP18C that utilizes the two central eyelets. In this example, the two tails T1, T2 of pattern SP18C extend out of the central eyelets and are coupled together. Note that a similar cross-sectional view of this configuration is also shown in FIG. 18F.

FIGS. 18D-G are schematic cross-sectional views showing some possible suture patterns that utilize one or more central eyelets. In FIGS. 18D-E, a single central eyelet 1821 is shown, and two possible patterns SP18D, SP18E are shown that utilize the central eyelet 1821. Variations of the suture patterns may also be possible which utilize both the central eyelet 1821 and the slots (not shown). In FIGS. 18F-G, two central eyelets 1822a, 1822b are formed in the traversing member and spaced apart from one another, and two possible patterns SP18F, SP18G are shown that utilize the eyelets. Variations of the suture patterns may also be possible which utilize two of the central eyelets and the slots (not shown).

Finally, in at least some examples, a combined clamp-washer may be used as shown in FIG. 19. Clamp 1900 may generally include the traditional elements of a pair of ring handles 1902 a ratchet 1904, a shank 1906, a pivot 1908 and jaw tips 1910. As shown, a retainer 1920 is unitarily formed with one of the jaw tips. Retainer 1920 may be formed of the same material (e.g., stainless steel) or a different material (e.g., a polymer) as the jaws, and may be coupled thereto or unitarily formed. This integrated configuration of clamp 1900 may allow for easier capture and manipulation of a suture SP19. As shown in the detailed view, the retainer 1920 is disposed slightly below the jaw tips 1910 such that a suture passing through the central opening in the retainer may be grasped between the two jaw tips of the clamp.

The disclosure above encompasses multiple distinct inventions with independent utility. While each or these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

The invention claimed is:

1. A method of wound closure comprising:
   providing a skin tensioning device having a rigid insert and an elastomeric shell, the skin tensioning device including a bridge body, a portion of the bridge body being in contact with a patient's skin and a second portion of the bridge body being elevated above a wound, the bridge body having a first leg including a first patient contacting surface configured to contact a patient's skin, a second leg spaced from the first leg and including a second patient contacting surface configured to contact the patient's skin, a first support connected to the first leg, a second support connect to the second leg, a first slot at least partially formed through a portion of the first leg, and a portion of the first support, a second slot at least partially formed through a portion of the second leg, and a portion of the second support, and a traversing member extending between the first support and the second support, and a traversing member extending between the first support and the second support;
   passing a suture through the skin tensioning device to stretch the patient's skin; and
   removing the skin tensioning device prior to closing the wound.

2. The method of claim 1, wherein passing a suture through the skin tensioning device comprises passing the suture through at least one side of the wound prior to passing the suture through at least one of the slots.

3. The method of claim 1, further comprising the step of successively applying tension on the suture and releasing the tension on the suture.

4. The method of claim 1, further comprising the step of maintaining tension on the suture for a duration of time to stretch the patient's skin.

5. The method of claim 1, further comprising the step of closing the wound with at least one of a suture, a staple or an adhesive.

6. A method of wound closure comprising:
   providing a bridge body having a rigid insert and an elastomeric shell, a portion of the bridge body being in contact with a patient's skin and a second portion of the bridge body being elevated above a wound;
   passing a suture through the bridge body;
   applying a force on the suture to partially flatten the bridge body; and
   removing the bridge body prior to closing the wound.

7. The method of claim 6, further comprising removing the force from the bridge body to allow the bridge body to return to a more elevated resting condition to gather tissue on opposite side of the wound and pull the tissue up toward the second portion of the bridge body.

8. The method of claim 6, further comprising the step of passing the suture through at least one side of the wound prior to passing the suture through the bridge body.

9. The method of claim 6, further comprising the step of placing the bridge body adjacent the wound.

10. The method of claim 6, further comprising the step of placing the bridge body across the wound so that portions of the bridge body are disposed on opposite sides of the wound.

11. The method of claim 6, further comprising the step of placing the second portion of the bridge body above the wound.

12. The method of claim 6, wherein applying a force on the suture comprises applying a force of greater than 4 Newtons to gather the wound.

13. The method of claim 6, wherein passing a suture through the bridge body includes twice passing the suture through the bridge body.

14. The method of claim 6, further comprising the step of maintaining tension on the suture for a duration of time to stretch the patient's skin.

15. The method of claim 14, wherein the duration of time is between 5 and 10 minutes.

16. The method of claim 6, further comprising the step of successively applying tension on the suture and removing the tension.

17. The method of claim 6, wherein providing a bridge body having a rigid insert and an elastomeric shell comprises providing a bridge body having an elastomeric shell that fully covers the rigid insert.

18. The method of claim 6, further comprising the step of closing the wound with at least one of a suture, a staple or an adhesive.

* * * * *